United States Patent [19]

Sufrin et al.

[11] Patent Number: 5,652,105

[45] Date of Patent: Jul. 29, 1997

[54] SUBSTRATE FOR DETECTION OF MAMMALIAN 5-C-DNA METHYLTRANSFERASE

[75] Inventors: Janice R. Sufrin, Amherst, N.Y.; Judith K. Christman, Elkhorn, Nebr.; Canio J. Marasco, Jr., Buffalo, N.Y.; Gholamreza Sheikhnejad, Detroit, Mich.

[73] Assignee: Health Research, Inc., Buffalo, N.Y.

[21] Appl. No.: 508,778

[22] Filed: Jul. 28, 1995

[51] Int. Cl.$^6$ .............................. C12Q 1/68; C07H 21/04
[52] U.S. Cl. .................................................. 435/6; 536/23.1
[58] Field of Search .............................. 435/6; 536/23.1

[56] References Cited

U.S. PATENT DOCUMENTS 5,503,975  4/1996  Smith et al. .............................. 435/6

FOREIGN PATENT DOCUMENTS 0 571 911 A2  1/1993  European Pat. Off. .

OTHER PUBLICATIONS

Issa, et al. "Increased Cytosine DNA–Methyltransferase Activity During Colon Cancer Progression" J. National Canc. Inst. vol. 85, No. 15, pp. 1235–1240, 1993.

Marasco, et al. "A Convenient Method for the Direct Incorporation of 5–Fluoro–2'–deoxycytidine into Oligodeoxynucleotides" J. Org. Chem, vol. 57 pp. 6363–6365, 1992.

Wainfan, et al. "Rapid Appearance of Hypomethylated DNA in Livers of Rats Fed Cancer–promoting, Methyl–deficient Diets" Cancer Research 49, pp. 4094–4097, 1989.

Bestor, et al. "Two DNA methyltransferases from murine Erythroleukemia cells: Purification, sequence spedivicity, and mode of interaction with DNA" Proc Natl Acad Sci 80, pp. 5559–5563, 1983.

Smith, et al. "Recognition of Unusual DNA Structures by Human DNA(cytosine–5)methyltransferase" J. Mol. Biol. 217 pp. 39–51, 1991.

Smith, et al. "Recognition of Foldback DNA by the Human DNA (Cytosine–5)–methyltransferase" Biochemistry, Bol. 31, No. 3, pp. 850–854, 1992.

Klimasauskas, et al. "HhaI Methyltransferase Flips Its Target Base Out of the DNA Helix" Cell, vol. 76, pp. 357–369, 1994.

Christman, et al. "5–Methyl–2'–deoxycytidine in single–stranded DNA can act in cis to signal de novo DNA methylation" Proc. Natl. Acad. Sci. vol. 92 pp. 1–5, 1995.

Abstract of Sheikhnejad, et al. "A novel Mechanisms for de novo Methylation of DNA is Suggested by Evidence that 5–methylcytosine [5mC] Residues in Specific Sites in ss–DNA direct methylation of Cytosine[C] Residues in Distant CpG sites" PAACR vol. 35, 1994.

Sheikhnejad, et al. "Elucidation of Sequence Recognition by Murine C5–DNA Methyltransferase Using Defined Oligonucleotide Substrates Containing 5–Methyl–Deoxycytidine and 5–Fluoro–Deoxycytidine at Specific Sites" Mol. & Cell. Diff. vol. 1, p. 383, 1993.

*Primary Examiner*—Douglas W. Robinson
*Assistant Examiner*—Thanda Wai
*Attorney, Agent, or Firm*—Michael L. Dunn

[57] ABSTRACT

A substrate selective for detection of mammalian 5-C-DNA methyltransferase in the presence of bacterial 5-C-DNA methyltransferase, said substrate comprising oligomeric DNA which contains at least one 5-methylcytosine residue, and at least one cytosine or 5-fluorocytosine residue, each of which are followed in linkage to a guanine residue. The invention also includes a method for measuring the presence of mammalian 5-C-DNA methyltransferase which comprises contacting a sample containing 5-C-DNA methyl transferase with the substrate and also includes a method for inhibiting mammalian 5-C-DNA methyltransferase which comprises contacting a sample containing 5-C-DNA methyl transferase with the substrate.

19 Claims, 3 Drawing Sheets

A.

1=C, 5mC; 2=G or Inosine (I); 3=C, site of methylation
4=G, I, O⁶-methyl G, C, A or an abasic site

SUBSTRATE FOR DETECTION OF MAMMALIAN 5-C-DNA METHYLTRANSFERASE

BACKGROUND OF THE INVENTION

This invention relates to materials and methods for the detection of DNA 5-cytosine methyltransferase (5-C-DNA methyltransferase) and more particularly relates to a novel oligodeoxyribonucleotide, i.e. ODN, as a substrate for selective detection and quantification of mammalian 5-C-DNA methyltransferase.

Regulation of gene expression in eukaryotic organisms involves many different biological mechanisms that operate independently of one another. DNA methylation is among these mechanisms associated with the regulation of gene expression. The enzyme which is responsible for this process, DNA methyltransferase, acts by transferring a methyl group from S-adenosylmethionine to a cytosine residue in a CG-sequence of DNA to give an altered sequence containing 5-methylcytosine. Not all CG sequences in DNA are methylated by the enzyme and not all DNA methyl transfer reactions are involved in gene expression, but there is a consistent, well-documented correlation between DNA methylation and the inhibition of the activity of many genes.

Attempts to clarify the role that DNA methylation plays in gene expression have been hampered by the lack of a specific inhibitor of DNA methyltransferase. In this regard, the compounds 5-azacytidine (azaC) and 5-aza-2'-deoxycytidine (azadC) have been used to study inhibition of DNA methylation. Both azaC and azadC are metabolized and are ultimately incorporated into cellular DNA. Subsequently, DNA which contains azadC directly inhibits DNA methyltransferase and thus, the overall process of DNA methylation. However, DNA which contains azadC also interferes with a variety of other DNA protein-interactions and so the cellular effects of azadC can not be ascribed solely to its ability to inhibit DNA methylation. There remains a need for the systematic design and synthesis of totally specific inhibitors of DNA methyltransferase.

For example, methylation of Cytosine (C) residues in DNA plays an important role in regulating gene expression during vertebrate embryonic development. Conversely, disruption of normal patterns of methylation is common in tumors and occurs early in progression of at least some human cancers. In vertebrates, it appears that the same DNA methyltransferase (DNA MTase) maintains pre-existing patterns of methylation during DNA replication and carries out de novo methylation to create new methylation patterns. There are several indications that inherent signals in DNA structure can act in vivo to initiate or block de novo methylation in adjacent DNA regions.

In vertebrate cells, about 3% of cytosine (C) residues in DNA have a methyl group on carbon 5 and 5-methyl cytosine (5 mC) is the only naturally occurring modified base so far detected in DNA. Enzymatic methylation of Cytosine residues in DNA occurs postreplicatively and primarily involves C residues in CpG dinucleotides, although methylation has been observed at C residues 5' of other nucleotides. The extent and pattern of methylation of genomic DNA is species- and tissue-specific, which implies that the pattern of methylation is faithfully inherited in all cells of common lineage within a tissue. Analysis of methylation patterns of specific genes during development suggests that patterns established in sperm and oocytes are lost during early development, that regions other than CpG islands become almost fully methylated, and that loss of methylation occurs at specific sites in tissues where a gene is expressed.

Although not all genes are regulated by methylation, hypomethylation at specific sites or in specific regions in a number of genes is correlated with active transcription. DNA methylation in vitro can prevent efficient transcription of genes in cell-free systems or transient expression of transfected genes; methylation of C residues in some specific cis-regulatory regions can also block or enhance binding of transcription factors or repressors. DNA methylation is involved in inactivation of one of the two X chromosomes in female mammalian somatic cells, and allele-specific methylation has been proposed as a factor in genomic imprinting. The most direct evidence for the importance of DNA methylation in development is the demonstration that homozygous mutation in murine DNA 5-cytosine methyltransferase (5-C-MTASE) leads to impaired embryonic development.

Conversely, disruption of normal patterns of DNA methylation has been linked to development of cancer. The 5-methylcytidine (5MeC) content of DNA from tumors and tumor-derived cell lines is generally lower than in normal tissues, although increased methylation of CpG sites occurs in some genes and chromosome regions. While these observations support the concept that methylation patterns are established in the embryo and altered during carcinogenesis by a combination of de novo methylation and loss of methylation in a time-, sequence-, and tissue-specific manner, the mechanism(s) by which these changes occur and are regulated with such apparent precision has not been defined.

The processes involved in regulating de novo methylation are particularly puzzling. As would be predicted for an enzyme that maintains established patterns of methylation during DNA replication, mammalian DNA MTases have a much greater capacity for methylating hemimethylated CpG sites in double-stranded (ds) DNA than completely unmethylated sites. However, since the gene encoding mammalian DNA 5-C-MTase is present as a single copy per haploid genome and there is no direct evidence for the existence of a separate de novo DNA MTase, it appears that the same enzyme must carry out both functions.

It should be pointed out that bacterial 5-C-DNA methyltransferases do not function in the same way as and are not the same as mammalian 5-C-DNA methyltransferases but do have sufficient similarity in mechanism that to date the presence of bacterial 5-C-DNA methyltransferase can interfere with detection methods for mammalian 5-C-DNA methyltransferase.

In any case, mammalian DNA methyltransferases are involved in gene expression and the activity of this enzyme is elevated in the colon mucosa of patients at risk for colon cancer. It has also been shown that lowering the level and activity of DNA 5-MTase also lowers the incidence of colon cancer in transgenic mice that develop this disease spontaneously. It is therefore important to be able to detect and quantify mammalian 5-C-DNA methyltransferases and distinguish them from other 5-C-DNA methyltransferases which cause different functional effects.

FIGS. 3–6 shows Seq. ID #7 in looped conformations.

Figure 8:
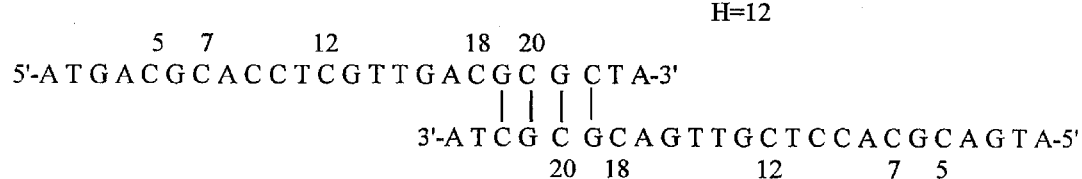
Figure 9:
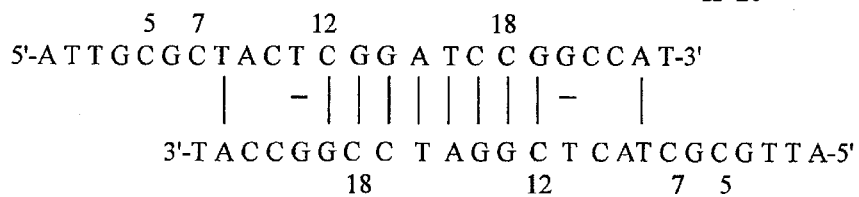

FIG. 8 shows Seq. ID #21 in a homodimer conformation.
FIG. 9 shows Seq. ID #22 in a homodimer conformation.

BRIEF DESCRIPTION OF THE INVENTION

In accordance with the present invention, a novel DNA analog has been developed which specifically interacts with mammalian 5-C-DNA methyl transferase. The DNA analog acts as a substrate for selective detection of mammalian 5-C-DNA methyl transferase even in the presence of bacterial 5-C-DNA methyl transferase. The substrate comprises oligomeric DNA (ODN), which contains at least one 5 methyl 2' deoxycytosine (5mC) residue, and at least one cytosine (c) or 5-fluorocytosine (5FC) residue, each of which are followed in linkage to a guanine (G) residue.

The novel substrates of the invention are single-stranded with the potential to form transient looped structures and preferably contain from 12 to 50 nucleic acid bases and at least two C residues, at least one of which is 5mC and at least one is a C in a nucleotidyl linkage to G (CG). This C may be C or, 5FC and modifications may be made in the sugar or phosphodiester moieties of the phosphodiester linkage to increase resistance of the ODN to nuclease digestion.

The design of the DNA analogs of the invention which specifically interact with mammalian DNA methyltransferase has several distinct advantages. In particular, the effects of these analogs are specifically ascribed to their effects on DNA methyltransferase and therefore the process of DNA methylation in cells. These analogs are useful as research tools to elucidate the basic mechanistic behavior of mammalian DNA methyltransferases and to provide a highly sensitive means to measure (or inhibit) DNA methyltransferase activity of tumor cells, whether obtained from established cell cultures or from clinically obtained tumor tissue samples. Furthermore, the technology exists to develop these DNA analogs as diagnostic tools for the premalignant state in cancer progression and for following responses to the treatment of cancers, and particularly, colon cancer.

Examples of particular embodiments of the invention include the following oligomeric DNA strands. For purposes of all sequences disclosed herein, to meet nucleotide sequence disclosure requirements R and N may both be represented by N.

| | |
|---|---|
| 5'-ATTGCGNATTNCGGATNRGCGATC-3' | (Seq. ID #1) |
| 5'-ATTGCGNATTCCGGATCRGCGATC-3' | (Seq. ID #2), and |
| 5'-ATTGNGCATTCCGGATCRGCGATC-3' | (Seq. ID #3) | where N is 5-methyl-cytosine and R is either cytosine or 5-fluoro-cytosine.

The related double-stranded substrates such as:

| | |
|---|---|
| 5'-ATTGNGCATTCNGGATCNGNCATC-3' | (Seq. ID #8) |
| 3'-TAARGCGTAAGGRCTAGGRGGTAG-5' | (Seq. ID #20) | where N is 5-methyl-cytosine and R is either cytosine or 5-fluoro-cytosine which act as matched control substrates, since they provide a highly sensitive means to measure (or inhibit) the activity both mammalian 5-C-DNA methyltransferase and those bacterial 5-C-DNA methyltransferases that recognize the specific order of residues in this substrate.

DETAILED DESCRIPTION OF THE INVENTION

"Oligomeric DNA" or ODN, as used herein, means a DNA having from 10 to 75 "purine or pyrimidine bases" connected in a series of nucleotides which are deoxyribonucleotides or analogs of deoxyribonucleotides with chemically modified sugars or linkages between sugars. Purine or pyrimidine bases as used herein mean adenine (A), cytosine (C), guanine (G), thymine (T), and analogs of C (5-methyl-cytosine, 5-fluoro-cytosine, 5-bromo-cytosine, etc.) that have been chemically modified so as to continue to be chemically acceptable into a synthetic chain of deoxyribonucleic acid or deoxyribonucleic acid analogs.

"5-C-DNA methyl transferase" means DNA 5-cytosine methyl transferase for methylation of cytosine to form a 5-methyl-2'-deoxycytosine residue in DNA.

To obtain DNA analogs which are highly specific for mammalian DNA methyltransferase, we have artificially constructed ODN analogs of DNA which contain CG sequences that have the intrinsic potential to be recognized and methylated by DNA methyltransferases. In general, we have chosen ODN constructs which are 24 bases in length, or 24mers, but our invention can also apply to ODNs that are shorter and/or longer than 24 bases in length e.g., 10 to 75 and preferably 12 to 50 bases in length. We have examined the activity of these ODNs as substrates for DNA methyltransferase, and have identified single-stranded as well as double-stranded constructs of DNA which are excellent substrates of DNA methyltransferase.

Four examples of DNA constructs are shown in Table 1. They are labeled Sense (S), Antisense (AS), Methylated Antisense 1 (M1) and Methylated Antisense 2 (M2). The mammalian DNA methyltransferase substrate activity of these 4 single-stranded ODNs is shown in Table 2. It can be seen that M2 has exceptional substrate activity, especially in comparison with S and AS, which were designed to have an optimal number of potentially methylatable CG sites available. In contrast to the remarkable substrate activity of $M_2$ for mammalian DNA methyltransferase, it is not methylated by most bacterial DNA methyltransferases which require double stranded DNA as a substrate. Even with bacterial SssI methyltransferase which has similar specificity to mammalian DNA methyltransferase in that it methylates CG and can methylate single stranded DNA, M2 has only moderate activity as a substrate (see Table 3). This property of $M_2$ provides an approach to accurately monitoring levels of DNA methyltransferase activity in clinically obtained tissue samples that might otherwise be contaminated by bacteria, since bacterial DNA methyltransferase activity would be excluded as a component of this measurement.

Three examples of double-stranded DNA analog constructs are shown in Table 4: S+AS, S+M1, and S+M2. Their activity as mammalian DNA methyltransferase substrates is also shown in this Table and it can be seen that the double-stranded ODN, S+M1 has exceptional substrate activity which is comparable to that observed for the single stranded ODN, M2.

Thus, we have artificially constructed and identified single-stranded ODN and double-stranded ODN, both with exceptional activity as substrates of mammalian DNA methyltransferase. To our knowledge, the composition (i.e. the exact base sequence) of these synthetic substrates is unique. In addition, to our knowledge, there are no other reports of methylated single stranded DNAs serving as exceptional substrates for mammalian DNA methyltransferase and, in particular, no previous example of substrate activity in oligomers with 5mC residues in sites other than CG sites. Since methylation occurs at a CG site distant from the 5mC residues, this substrate is undergoing de novo methylation.

It is known to those skilled in the art that double-stranded DNAs including double stranded ODNs with multiple 5mCGs in one strand base-paired with CGs in the complementary strand are substrates for mammalian DNA methyltransferases and we do not consider this aspect of our invention proprietary. The characteristics of the double-stranded ODNs described here that are considered unique are 1) their sequence which is unique in that at least one ODN of the double stranded ODN is an excellent substrate for mammalian but not bacterial methyl transferases and 2) their design which renders them as substrates for both mammalian and specific bacterial DNA methyltransferases when present in the double stranded form, 3) their extremely high substrate activity for mammalian 5-C-methyltransferases. These double-stranded ODNs also serve as unique controls for the single-stranded ODNs that are the invention in that they will detect both mammalian and other methyltransferases present in test samples while the matched single-stranded ODN will detect only the mammalian enzyme.

In order to obtain highly potent inhibitors of mammalian DNA methyltransferase, we have selected ODNs with exceptional activity as substrates of DNA methyltransferase and have modified them by systematically replacing the C of each CG sequence with 5-fluoro-cytosine (FC), an analog of cytosine which cannot be methylated and which furthermore, can react irreversibly with the enzyme in a manner which leads to inhibition of the DNA methyltransferase. This strategy is illustrated in Table 5 which shows how the double stranded DNA analog substrate of DNA methyltransferase, S+M1, was systematically modified by the replacement of FC for C in this ODN, to produce a series of FC-modified ODNs of S+M1, for testing as potential inhibitors of DNA methyltransferase.

Table 6 illustrates how this strategy was applied to another ODN substrate of DNA methyltransferase, which we have designated as ASM7. The systematic substitution of FC for C in this ODN led to a series of FC-modified ODNs. From this series, a potent DNA methyltransferase inhibitor, ASM7F18, was identified.

Thus, we have systematically modified substrates of DNA methyltransferase, by substituting FC for C in CG sequences, to construct potent inhibitors of DNA methyltransferase.

A unique aspect of our invention is that the ODNs we have developed will provide a means to measure active enzyme in complex mixtures of proteins typical of cells and cell extracts. This contrasts to the use of antibodies for detecting enzyme, a method which measures both active and inactive enzyme, and cannot distinguish the active component. This contrasts also to methods which measure mRNA content which cannot be used to quantitate the amount of active enzyme protein.

ODNs of the invention which we have prepared contain 5-methyl-cytosine (5-meC) in addition to the standard bases (A,T,G,C). These ODNs can be prepared routinely on a DNA synthesizer.

Some ODNs we have prepared for purposes of comparison contain only standard bases (A,T,G,C) and can be prepared routinely on a DNA synthesizer.

Some ODNs we have prepared contain 5-fluoro-cytosine (5FC) in addition to the standard bases (A,T,G,C) and 5-meC. We have developed a simple and convenient method for incorporating FC into ODNs and have published these procedures which we do not consider proprietary and are now well known to those skilled in the art.

The substrates of the invention have numerous utilities and may, for example, be used as:

1. substrates for evaluating levels of enzyme in experimental systems either by direct measurement of enzyme activity or by quantitating covalent complex formation with ODNs containing FC;
2. reagents for specifically inhibiting DNA methyltransferase, as opposed to other methyltransferases in crude cell extracts or in cells in culture or in animal models;
3. reagents for detecting the presence of as yet uncharacterized CG methyltransferases and for determining sequence specificity of these enzymes or for determining which sites in known sequences are methylated (i.e., by inserting FdC in different positions);
4. reagents for isolating and purifying DNA methyltransferases from cells or tissues. Biotinylated or tethered ODNs containing FC would be used for this application;
5. agents for differentiation therapy;
6. diagnostic tools where accurate measurement of DNA methyltransferase activity in clinically obtained tissue samples can be indicators of the extent of disease progression in carcinomas or alternatively as an indicator of therapeutic responses; and
7. probes for in situ detection of active DNA methyltransferase in frozen sections. This would be accomplished using biotinylated ODNs containing FC. Avidin linked alkaline phosphatase or peroxidase would then be reacted with the bound biotinylated ODNs to allow use of standard histochemical techniques for identifying cells or areas in tissues and/or tumors with high and low levels of active DNA methyltransferase.

Single-stranded ODNs of the invention with high specificity for mammalian DNA methyltransferase and their sequence-related double-stranded ODNs with high substrate activity for both mammalian and bacterial DNA methyltransferases have broad based general utility. Certain instances of the utility of these ODNs involve assays done using whole cells or tissue samples (i.e., colon) and so it is essential that these single-stranded and double-stranded ODNs (substrates and inhibitors) with high specificity for cell free preparations of DNA methyltransferase, also demonstrate similar activity as substrates and/or inhibitors of DNA methyltransferase in whole cells. Consequently, we have undertaken experiments to determine whether these ODNs 1) can enter whole cells and 2) are active against DNA methyltransferase in whole cells. For these experiments, several ODNs were synthesized that are end capped with phosphorothioate linkages, a standard procedure used to increase resistance of ODNs to degradation by cellular nucleases. Resulting data supports the proposition that capping with phosphorothioate linkages does not adversely affect the ability of oligomer A to inhibit methylation by DNA methyltransferase (using standard cell free enzyme assay) and in fact, capping appears to stimulate the rate of methylation of oligomer D ($ASM_7$) by more than 50% (Compare activity of D and C) (Table 7). Incorporation of FC in position 18 of oligomer A inhibits this methylation by 97% as would be predicted when covalent complexes are formed with DNA methyltransferase.

Having established that specific phosphorothioate end capped ODNs retain activity against DNA methyltransferase, their biological effects were examined in intact Friend cells: the biological effects of oligomer A were compared to oligomer B which has no available substrate sites and thus cannot be an inhibitor of DNA methyltransferase, and of oligomer D with oligomer C which has no FC.

A test was conducted to determine if these oligomers affect growth or differentiation of Friend leukemia cells. If growth effects are due to the toxicity of FC released from oligomers, then oligomer A and oligomer B should have equivalent effects and oligomer C should have no effect on growth.

Alternatively, if growth effects are due to an effect on methylation, then oligomer B which has no substrate site should be inactive and oligomer A which has FC in the primary substrate site should be active. Oligomer C may have a minor effect if it competes with endogenous DNA for DNA methyltransferase binding in a reversible manner. If, however, growth effects are due to a generalized effect of high oligomer concentration, then all oligomers, A, B and C, should affect growth similarly.

When cells were treated with 5mM concentrations of oligomers, it was seen that in fact oligomer A is more potent that B in inhibiting growth and that oligomer C has no appreciable effect on inhibiting growth. These results are consistent with the idea that the oligomers are taken up by the cells and that growth effects are due in part to an effect on methylation since oligomer A is more potent than oligomer B.

The single-stranded ODN we have designated $M_2$ is a "super substrate" for mammalian but not bacterial DNA methyltransferase. We believe the composition of this and related artificially constructed single-stranded substrates with loop forming potential such as ASM5, ASM7 to be unique. Unlike other known single-stranded substrates used for in vitro assessment of enzyme activity, these substrates appear to interact with both an activation and a catalytic site on the enzyme. There is currently a push to monitor levels of DNA methyltransferase in colon because of evidence from Baylin et al. (Increased Cytosine DNA-Methyltransferase Activity During Colon Cancer Progression, JNCI, 85, 1235, 1993) that the activity of this enzyme is increased in colon mucosa of patients at high risk for cancer, i.e., 50% of patients with familial polyposis had elevated levels of DNA methyltransferase (1.4-fold) and with colon cancers had 3 fold elevations. Since the assay is carried out using whole homogenized colon tissue, the possibility for false positives due to bacterial contamination is great. Our $M_2$ substrate would obviate this problem. The $M_2$ substrate and its 5-fluoro-2'-deoxycytidine containing analog and other functionally related substrates and their use in diagnostic assays for DNA methyltransferase are considered unique.

We have synthesized both single-stranded and double-stranded ODNs substituted with methyl deoxycytosine and fluoro deoxycytosine that inhibit DNA methylation and are capable of forming covalent complexes with DNA methyltransferases. The design of ODNs to inhibit two distinct DNA methylation processes, de novo methylation or maintenance methylation are unique. These ODNs are useful in determining the substrate specificity and mechanism of action of enzymes. The use of such ODNs for (a) quantitation of active enzyme by an assay that would be simpler than those previously developed and would involve filter-binding of radiolabeled or enzyme-linked DNA containing FdC; (b) isolation of enzymes from different sources by using biotinylated ODNs or ODNs linked to chromatography matrices; and (c) specific inhibitors of de novo enzymes in vivo are unique. Such inhibitors will be of great importance in development of gene therapy, since many genes are shut off by methylation after uptake into cells. These ODNs could also be useful in treating specific cancers, since inhibition of DNA methylation has been shown to cause differentiation of certain types of tumor cells.

The phosphoramidite of 5-fluorodeoxycytidine (5FdC) and unmodified 5-methyl deoxycytosine (5MdC) and 5FC-containing ODNs were synthesized and purified as described in Marasco, C. J. et al., J. Org. Chem. 57, 6363–6365 (1992). 5MdC phosphoramidite is commercially available. ss ODNs were heated to 90° C. for 10 min and quickly chilled on ice immediately prior to assay. The ss ODNs were not substrates for Hpa II or Hha I DNA methyltransferases (MTases) at 37° C., indicating an absence of stable intermolecular ds regions. For ds ODNs, an equimolar mixture of complementary ODNs was heated to 90° C. for 10 min and slowly cooled to room temperature. These ds ODNs were susceptible to quantitative cleavage by Hpa II or Hha I when their recognition sites contained no 5MeC.

Preparation of Murine DNA 5-C-MTase. The DNA 5-C-MTase used in these studies was the 100,000×g supernatant of a 0.3M NaCl extract of Friend erythroleukemia cell nuclei. All procedures were described in Wainfan et al., Cancer Res. 49, 4094–4097 (1989), except for the addition of 5 µg each of antipain dihydrochloride, leupeptin, chymostatin, and pepstatin (Boehringer Mannheim) to the extraction buffer.

Methylation Assay. Reaction mixtures (50 µl) in 0.1M imidazole, pH 7.4/20 mM EDTA/0.5 mM dithiothreitol contained 0.5 µg of each ODN indicated, ≈0.6 units of DNA 5-C-MTase (1 unit transfers 1 pmol to A (AS)·A'$M_p$ (M1) per min; see Table 7), and 2.8 µCi (1 Ci=37 GBq) of [methyl-$^3$H]AdoMet (AdoMet=S-adenosylmethionine) (8 µM). Substrate C sites are in excess in the reaction, and methyl transfer is linear for >45 min. For accuracy, methylation rates <5 pmol/30 min were measured in quadrupled reaction mixtures (200 µl). After incubation for 30 min at 37° C., ODNs were processed for quantitation of radiolabel as described (20) with 25 µg of salmon sperm DNA added as carrier prior to perchloric acid precipitation.

ODNs A (AS) and A' (S) (Table 8) were tested for their ability to act as substrates for methylation by murine DNA 5-C-MTase by measuring the initial rate of methyl transfer from [methyl-$^3$H]AdoMet to these ODNs with substrate in excess. Neither A nor A' was efficiently methylated in the ss form, although A was methylated at almost three times the rate of A' (Table 8). Since A and A' have the same number and spacing of CpG sites, this indicates that the density and spacing of CpG sites are not sufficient to establish the rate of methylation. When A and A' were annealed to form an unmethylated ds ODN substrate, the rate of methylation was no higher than that obtained with A' alone, even though twice as many sites per mole of substrate were available for methylation.

All assays were performed in duplicate. Values shown are the average incorporation in three assays± SD and represent the initial rate of methylation-i.e., incorporation of [$^3$H]CH$_3$ into DNA, during a 30 min. incubation carried out and quantitated as described in Materials and Methods. With hemimethylated substrates (lines 4 and 5), ≈10% of available CpG sites were methylated in 30 min. Background incorporation in the absence of substrate was about 500 dpm., rate equals rate of methylation relative to A1 and ND equals, not detected.

When either A or A' in the ds ODN contained 5MeC residues in place of all C residues in CpG sites forming hemimethylated sites ($M_p$), the rate of methylation of the unmethylated strand was increased >130-fold relative to the rate of methylation of A in the ss form (compare line 1 with lines 4 and 5 in Table 8). No methylation of completely methylated substrate could be detected, and substitution of 5MeC for C in non-CpG sites ($M_x$) in the ds ODNs did not stimulate the rate of methylation significantly above that of completely unmethylated substrate (compare line 3 with lines 7 and 8 in Table 8). Thus, the interaction of murine DNA 5-C-MTase with A and A' in ss and ds forms does not differ detectably from its interaction with longer ss- and dsDNA substrates; i.e., hemimethylated DNA is methylated much more efficiently than completely unmethylated ds- or ssDNA (Bestor, et al., Proc. Natl. Acad. Sci., USA 80, 5559–5563 (1983)). The results also demonstrate that 5MeC in non-CpG sites fails to stimulate methylation of dsDNA, even when potential methylation sites (CpG sites) are no more than one or two base pairs distant.

In contrast, substitution of a 5MeC residue(s) for a C residue(s) in different sites in ss ODNs had widely varying effects on the rate of methylation (Table 9, rate in the tables is the rate of methylation relative to A (0.15±0.01 pmol of [methyl$^3$ H] Ado Met per 30 min., ND=non detectable). 5MeC in all CpG sites in either A or A' (ODN A and A', lines 2 in Table 9, effectively blocked methyl transfer, which is predictable if all methylation occurs at C residues in CpG sites. However, substitution of 5MeC for all C residues next to other nucleotides had a markedly different effect on methylation of ss and ds ODNs. The rates of methylation of ss ODNs A and A' increased dramatically, approaching or surpassing those of hemimethylated ds ODNs (compare lines 4 and 5 in Table 8 with line 3 in Table 9); again A was the better substrate (Table 9, lines 3). Since 5MeC substituted for C in non-CpG sites had no effect on methylation rates of ds ODNs (Table 8, lines 7 and 8), this suggests that 5MeC in ssDNA can stimulate methylation of CpG sites in cis.

To determine which specific 5MeC residues stimulate methylation, derivatives of A (AS) and A' (S) were synthesized with single substitutions of 5MeC for C. A single 5MeC near the 5' end of ODN A, replacing either the C residue in position 5 (C5) or position 7 (C7), stimulated methylation as effectively as the three 5MeC residues replacing C7, C11, and C17 of ODN A (Table 9, compare lines 3–5; ODN A). In contrast, A strands with 5MeC residues substituted for C residues in other sites were only marginally better substrates than unmethylated A strands. The exception was a 5MeC in position 18, which increased the rate of methylation of A ≈12-fold (Table 9, line 7; ODN A). These results confirmed that 5MeC residues in ss ODN substrates do not have to be in a CpG site to activate methylation. Introduction of 5MeC residues into A' demonstrated that the presence of a 5MeC residue near the 5' end of an ODN is not in itself sufficient to increase the initial rate of methylation (Table 9, line 4; ODN A') and that 5MeC residues in the middle (lines 5 and 7; ODN A') or at the 3' end (line 9; ODN A') of an ODN can also activate methylation. Clearly, factors other than density of 5MeC residues or their position relative to the 5' end are important in determining which 5MeC residues can serve as activators of methylation.

Substitution of C residues with 5FC was used to determine which sites become substrates for enzymatic methylation in A strands containing 5MeC. It has been shown that both bacterial and mammalian DNA 5-C-MTases form stable covalent linkages with 5FC residues in DNA during the process of methylation. Under conditions of substrate excess, this leads to rapid inactivation of the enzymes. We have found that (i) stable covalent complexes between murine DNA 5-C-MTase and 5FC residues are only formed when 5FC residues are in substrate CpG sites, and (ii) our DNA MTase extracts contain only one species of protein (≈190 kDa) that forms covalent complexes in an AdoMet-dependent manner with ODNs with 5FC in substrate sites. 5FC substitution for C residues in all CpG sites (C residues at positions 5, 12, 18, and 20) of $AM_x$ completely inhibited methylation, reconfirming that C residues in CpG dinucleotides are substrates (Table 10, line 3). Single substitutions of 5FC for C5, C1, and C20, had little effect on the rate of methylation of $AM_x$, whereas substitution of 5FC for C18 almost completely inhibited methylation (Table 10, line 5). The same result was obtained with A ODNs containing a single 5MeC in position 5 or 7; i.e., 5FC in position 18 completely inhibited methylation while 5FC in position 20 had no effect on the rate of methylation (Table 10, lines 9, 10, 12, and 13). Thus, 5MeC in position 5 or 7 activates DNA 5-C-MTase to methylate C18 while failing to activate methylation of a C residue only two bases downstream. Since the distance between C5 and C18 and between C7 and C20 is the same, this result suggests a very specific relationship between DNA structure and/or sequence and the recognition of substrate sites in ssDNA that is not strictly related to distance between sites. It can also be concluded (i) that 5MeC residues can activate methylation of both ss- and dsDNA and that in both cases the substrate C residue is in a CpG site; (ii) that in completely dsDNA, 5MeC residues must be located in CpG sites either to block the use of DNA as a substrate or to activate methylation (Table 8); and (iii) that in ssDNA, 5MeC residues must be in CpG sites to block methylation (compare ODN A', lines 5 and 10 and ODN A and A', lines 2 in Table 8) but not to serve as activators of methylation.

Figure 1:
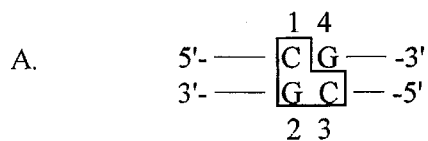
FIG. 1 shows a hypothetical recognition site for mammalian DNA methyltransferase.
Figure 2:
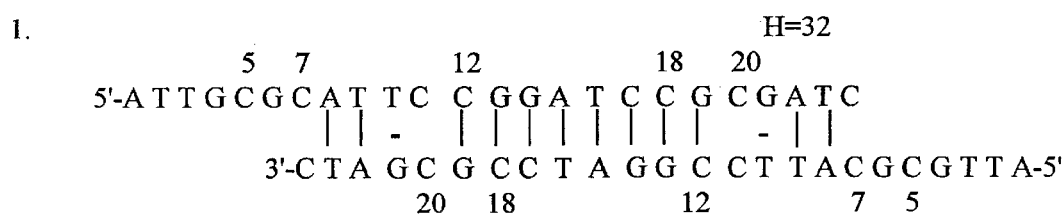
FIG. 2 shows Seq. ID #7 in a homodimer conformation.
Figure 3:
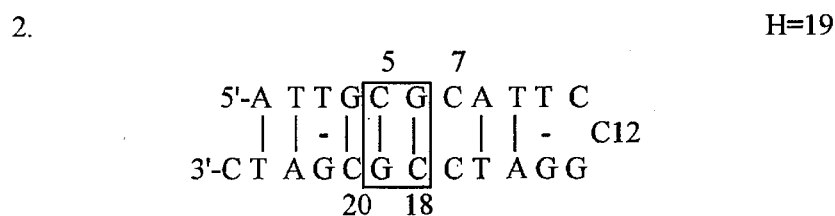

Smith et al. (J. Mol. Biol. 17, 39–51 [1991] and Biochemistry 31, 850–854 [1992]), have previously noted that in dsDNA substrates or in ssDNAs where the substrate CpG site is present in the ds stem of a long-stemmed stem-loop structure, the substrate C residue for mammalian DNA 5-C-MTase must be in a CpG site but need not be base paired to a G residue in the complementary strand. A search for similar recognition sites in potential inter- and intramolecular hydrogen-bonded structures that can be formed by ODN A (FIG. 1) was made using the STEMLOOP function of the Genetics Computer Group package (Version 7.3.1-UNIX; September 1993) and the self-complementarity function of OLIGO (Version 3.4; National Biosciences, Hamel, Minn.). The structures generated by these programs indicated that ODN A could form a homodimer with 32 hydrogen bonds and a variety of stem-loop structures. There are six potential stem loops stabilized by at least 3 adjacent base pairs. Those with more than 9 hydrogen bands or those with C7 positioned to direct methylation at C18 or C20 is shown in the drawings. Neither 5MeC in position 5 nor 5MeC in position 7 is in a base-paired region in the homodimer non-loop structure or in base stem-loop (structures 3 and 4, FIGS. 4 and 5). The structure, which contains a 10-bp-long stem stabilized by 19 hydrogen bonds (Structure 2, FIG. 3) has a base-paired CpG site in the stem. When 5MeC is substituted for C5 in this site, a hemimethylated recognition site for DNA 5-C-MTase is formed with C18. No methylation of the C20 in structure 2 would be predicted, since C20G21 is paired with T3G4 and, thus, is not in a recognition site. Theoretically, a 5MeC in position 18 in structure 2 or 3 (FIGS. 3 and 4) could activate methylation at C5 or C12, respectively. In this regard, it is of interest that 5MeC in position 18 does activate methylation of A, although with less efficiency than 5MeC in position 5 or 7. Structures 1–4 do not, however, explain how 5MeC in position 7 can activate methylation at C18. Only one structure (5), shown in FIG. 6, has a stem-loop C18 positioned in a substrate recognition site containing 5MeC in position 7. It has a 3-bp-long stem, with only 9 hydrogen bonds, and has the substrate C18 in a non-base-paired position. X-ray diffraction studies of the structure of DNA in the active site of a bacterial DNA 5-C-MTase (Hha I) have recently been reported (Klimasauskas et al., Cell 76, 357–369 (1994)). They demonstrate that hydrogen bonds between the substrate C residue and the G residue in the complementary strand are broken; the C residue is swung out of the helix, allowing methylation to occur. This may explain why substrate C residues that cannot be base paired are particularly good methyl acceptors, since their rotation out of the helix requires less energy than rotation of normally hydrogen-bonded C residues. In this regard, it should be noted that 5MeC in position 5 in structure 5 could potentially direct methylation at C20. However, no catalytic interaction was detected between murine DNA 5-C-MTase and A with 5MeC in position 5 and 5FC in position 20 (Table 10, line 10). This suggests a preferential binding of the MTase to the "mismatched" recognition site formed by hydrogen bonding between 5MeC in position 7 and G19 over the fully base paired recognition site formed by hydrogen bonding between 5MeC5G6 and C20G2.

Figure 7:
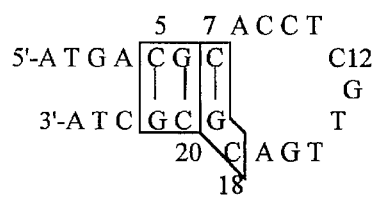
FIG. 7 shows Seq. ID #21 in a loop homodimer conformation.

Although we do not have direct evidence for formation of these looped structures and cannot rule out the possibility that the computer algorithms used failed to detect some potential substrate sites with non-Watson-Crick pairing, the structures discussed allowed design of additional ODNs to test the hypothesis that formation of a loop with a mismatched recognition site is necessary for 5MeC in position 7 to direct methylation at C18. Two ODNs with approximately the same base composition, a 5MeC in position 7, and the same number and spacing of CpG sites as ODN A were synthesized. One ODN (structure 6, FIG. 7) forms a stem-loop of the same size with the same relationship between C7 and C18 as A (structure 5, FIG. 6). It can also form a homodimer that is stabilized by 12 hydrogen bonds (structure 7, FIG. 8) with the substrate C18 in a ds region but not in a hemimethylated site. The other ODN forms a homodimer with 28 hydrogen bonds (structure 8, FIG. 9) and five stem-loop structures stabilized by at least three adjacent hydrogen-bonded base pairs. C7 is not base-paired in any of these structures. However, it cannot form a stem-loop structure analogous to structures 5 and 6. This ODN is methylated at the same rate as unmethylated A, whereas the ODN that can potentially form structure 6 is methylated at >300 times the rate of unmethylated A.

Since little or no methylation of CpG sites (including C18) occurs when they are in an unmethylated ds ODN (A·A') or a ds ODN containing 5MeC in non-CpG sites including C7 (Table 7, lines 3, 7, and 8), it can be concluded from the data presented here that a stem-loop structure may be both necessary and sufficient to allow 5MeC in position 7 to direct methylation at a site 12 bases downstream. However, it is unlikely that such a stem-loop structure, containing only nine hydrogen bonds would exist in solution at 37° C. unless it is stabilized by its interaction with DNA 5-C-MTase, perhaps with the aid of other nuclear proteins present in our extracts.

The model proposed is consistent with our results. This model posits that the active site in mammalian DNA 5-C-MTase contains both a regulatory region and a catalytic site. The regulatory region limits the rate of methyl transfer at the catalytic site. Interaction between 5MeC and the regulatory region relieves this inhibition, leading to an increased rate of methylation of a substrate C residue. In dsDNA, activation occurs primarily at hemimethylated recognition sites in which the substrate C need not be hydrogen bonded to a G in the complementary strand (Smith et al., Biochemistry 31, 850–854 (1992)). Our results indicate that 5MeC in a looped ssDNA can also activate methylation of a substrate C residue in instances that allow DNA to form a structure in the active site analogous to the recognition sites for DNA 5-C-MTase in dsDNA (structures 2, 5, and 6). Based on this model, our results would further suggest that a short ds region of 3 bp including a base pair between the 5MeC residue and the G residue in the substrate CpG site is sufficient to activate methylation but only when the C to be methylated is not hydrogen bonded to a G.

If one assumes that ss regions in larger DNA molecules can form similar looped structures in the active site of DNA MTase, it is evident that this mechanism could account for methylation of CpG sites at some distance from an established methylation site. Methylation would occur in cis through formation of recognition sites in stem-loops and might also occur in trans when ss loops from different DNA molecules or regions are brought close enough in the nucleus to form recognition sites, ss regions in DNA occur during the course of normal DNA replication and repair and may also be available as a result of "melting out" of DNA regions through protein binding or through formation of cruciform structures. When a ss region is converted back to dsDNA, through reannealing with its complement or through replication, a hemimethylated recognition site is formed, which is then a substrate for maintenance methylation. While the proposed mechanism is supported by observations that de novo methylation of integrated viral genomes or repeat elements can spread from a founder site, further studies will be required to confirm that 5MeC in ss regions of DNA can actually activate methylation at distant sites in DNA of living cells. It will also be of interest to examine the possibility that the small percentage of 5MeC residues that are not in CpG sites in mammalian DNA influence the extent of methylation at adjacent CpG sites and to determine whether these 5MeC residues indicate the existence of a directive mechanism for de novo methylation mediated by additional DNA MTases or simply random errors introduced by normal DNA 5-C-MTase with relaxed specificity due to posttranslational modification or partial proteolytic degradation.

In summary, our results provide evidence for a mechanism whereby the single DNA 5-C-MTase found in mammalian cells can be as active in directing de novo methylation as it is in maintaining established patterns of methylation. They also suggest a rationale for hypothesizing that the specificity required for establishing tissue-specific patterns of methylation is determined by a combination of inherent factors that include the ability of particular sequences to form the required stem-loop structures in ssDNA, the lifetime of the single-stranded state, and the availability of proteins to stabilize or destabilize particular looped structures.

TABLE 1

DNA ANALOG CONSTRUCTS

| | | |
|---|---|---|
| SENSE (S): | 3' TAACGCGTAAGGCCTAGGCGCTAG 5' | Seq. ID #6 |
| ANTISENSE (AS): | 5' ATTGCGCATTCCGGATCCGCGATC 3' | Seq. ID #7 |
| METHYLATED AS (M1): | 5' ATTGNGCATTCNGGATCNGNGATC 3' | Seq. ID #8 |
| METHYLATED AS (M2): | 5' ATTGCGNATTNCGGATNCGCGATC 3' | Seq. ID #9 |

N = 5-METHYLCYTOSINE
Underlined sites function as substrate sites for the indicated bacterial DNA methyltransferase but only in double standed ODNs

TABLE 2

DNA METHYLASE SUBSTRATE ACTIVITY OF DNA ANALOG CONSTRUCTS

| DNA ANALOG | ACTIVITY (CPM) |
|---|---|
| BACKGROUND | 2691 |
| S | 4843 |
| AS | 12341 |
| M1 | 5487 |
| M2 | 882284 |

RESULTS ARE AVERAGE OF 2 EXPTS. ENZYME PREPARATION FROM FRIEND LEUKEMIA CELLS. ASSAYED WITH 1 μG OLIGOMER

TABLE 3

DNA METHYLASE SUBSTRATE ACTIVITY OF DNA ANALOG CONSTRUCTS

| DNA ANALOG | ACTIVITY (CPM) |
|---|---|
| BACKGROUND | 1351 |
| S | 175225 |
| AS | 49282 |
| M1 | 2339 |
| M2 | 51047 |

RESULTS ARE AVERAGE OF 2 EXPTS. BACTERIAL SSS1 ENZYME PREPARATION. ASSAYED WITH 0.25 μG OLIGOMER.

TABLE 4

DNA METHYLASE (FL) SUBSTRATE ACTIVITY OF DOUBLE STRANDED DNA ANALOG CONSTRUCTS

| DNA ANALOG | ACTIVITY (CPM) |
|---|---|
| BACKGROUND | 1813 |
| S | 1598 |
| AS | 1936 |
| M1 | 1373 |
| M2 | 157027 |
| S + AS | 2623 |
| S + M1 | 125686 |
| S + M2 | 9215 |

RESULTS ARE AVERAGE OF 2 EXPTS.

DOUBLE STRANDED DNA ANALOG CONSTRUCTS:

| | | |
|---|---|---|
| S | 5' GATCGCGGATCCGGAATGCGCAAT 3' | Seq. ID #6 |
| AS | 3' CTAGCGCCTAGGCCTTACGCGTTA 5' | Seq. ID #7 |
| S | 5' GATCGCGGATCCGGAATGCGCAAT 3' | Seq. ID #6 |
| M1 | 3' CTAGNGNCTAGGNCTTACGNGTTA 5' | Seq. ID #8 |
| S | 5' GATCGCGGATCCGGAATGCGCAAT 3' | Seq. ID #6 |
| M2 | 3' CTAGCGCNTAGGCNTTANGCGTTA 5' | Seq. ID #9 |

N = 5-methylcytosine

TABLE 5

DOUBLE STRANDED DNA ANALOGS BASED ON S + M1 AS POTENTIAL INHIBITORS OF DNA METHYLASE (FL)

| S + M1 | | ACTIVITY (cpm) | |
|---|---|---|---|
| S | 3' GATCGCGGATCCGGAATGCGCAAT 3' | 140,000 | Seq. ID #6 |
| M1 | 3' CTAGNGNCTAGGNCTTACGNGTTA 5' | | Seq. ID #8 |
| | 5-FLUOROCYTOSINE CONTAINING ANALOGS OF S + M1 | | |
| | 5' GATNGCGGATCCGGAATGCGCAAT 3' | ND | Seq. ID #10 |
| | 3' CTAGNGNCTAGGNCTTACGNGTTA 5' | | Seq. ID #8 |
| | 5' GATCGNGGATCCGGAATGCGCAAT 3' | ND | Seq. ID #11 |
| | 3' CTAGNGNCTAGGNCTTACGNGTTA 5' | | Seq. ID #8 |
| | 5' GATCGCGGATNCGGAATGCGCAAT 3' | 140,000 | Seq. ID #12 |
| | 3' CTAGNGNCTAGGNCTTACGNGTTA 5' | | Seq. ID #8 |
| | 5' GATCGCGGATCNGGAATGCGCAAT 3' | 28,000 | Seq. ID #13 |
| | 3' CTAGNGNCTAGGNCTTACGNGTTA 5' | | Seq. ID #8 |
| | 5' GATCGCGGATCCGGAATGNGCAAT 3' | 36,000 | Seq. ID #14 |
| | 3' CTAGNGNCTAGGNCTTACGNGTTA 5' | | Seq. ID #8 |

IN THE SEQUENCES BEGINNING WITH 5', N = 5-FLUOROCYTOSINE.
IN THE SEQUENCES BEGINNING WITH 3', N = 5-METHYLCYTOSINE.

TABLE 6

| | SINGLE-STRANDED ODN | RELATIVE ACTIVITY[a] | |
|---|---|---|---|
| AS | 5' ATTGCGCATTCCGGATCCGCGATC 3' | 1 | Seq. ID #7 |
| ASM$_7$ | 5' ATTGCGNATTCCGGATCCGCGATC 3' | 170 | Seq. ID #15 |
| ASM$_7$F$_{18}$ | 5' ATTGCGNATTCCGGATCRGCGATC 3' | 3 | Seq. ID #2 |

[a]Rate of methylation relative to an equal amount of AS
N = 5-METHYLCYTOSINE  R = 5-flurocytosine

TABLE 7

ACTIVITY OF PHOSPHOROTHIOATE END CAPPED OLIGOMERS AS SUBSTRATES OR INHIBITORS OF DNA METHYLTRANSFERASE

| Oligomer | Structure | Rate of methylation (cpm/μg oligo/30 min) | |
|---|---|---|---|
| A* (capped ASM7F18) | ATTGCGNATTCCGGATCNGCGATC | 3,310 | Seq. ID #16 |
| B** | ATGGGATCCCATGGGTTNCCNATC | — | Seq. ID #17 |
| C (capped ASM7) | ATTGCGNATTCCGGATCCGCGATC | 114,760 | Seq. ID #18 |
| D (ASM7) | ATTGCGNATTCCGGATCCGCGATC | 72,010 | Seq. ID #19 |

*Proposed active oligomer
**same base composition but no methylatable CG site
N (first occurrence) = Methylcytosine
N (second occurrence) = 5 Flurocytosine

TABLE 8

Comparison of the rates of methylation of ss and ds ODNs by murine DNA C-5-MTase

| ODN | Initial rate, pmol/30 min | rate |
|---|---|---|
| Unmethylated substrates (de novo methylation) | | |
| A | 0.14 ± 0.01 | 1 |
| A' | 0.05 ± 0.01 | 0.35 |
| A · A' | 0.05 ± 0.01 | 0.35 |
| Hemimethylated substrates (maintenance methylation) | | |
| A · A'M$_p$ | 18.6 ± 2.61 | 133 |
| AM$_p$ · A' | 19.2 ± 1.2 | 138 |
| AMp · A'M$_p$ | ND | — |
| A · A'M | 0.05 ± 0.005 | 0.35 |
| AM · A' | 0.09 ± 0.01 | 0.64 |

A is 5'-ATTGCGCATTCCGGATCCGCGATC-3' = AS = Antisense;
A' IS 3'-TAACGCGTAAGG-CCTAGGCGCTAG-5' = S = Sense.
M$_p$ and M indicate 5MeC in place of all boldfaced or underlined C residues, respectively. A · A'M$_p$ = AS + M$_3$; Am$_p$ · A' = M$_1$ + S; AM$_x$ · A' = M$_2$ + S; A · A'M$_x$ = AS + M$_4$

TABLE 9

| SITES | SUBSTITUTION | RATE | |
|---|---|---|---|
| | ODN A | A = AS | |
| 1. | none | 1 | |
| 2. | 5, 12, 18, 20 | ND = M$_1$ = AM$_p$ | |
| 3. | 7, 11, 17 | 130 = M$_2$ = AM$_x$ | |
| 4. | 5 | 175 = ASM$_5$ | |
| 5. | 7 | 140 = ASM$_7$ | |
| 6. | 17 | 3.5 = ASM$_{17}$ | |
| 7. | 18 | 12 = ASM$_{18}$ | |
| 8. | 20 | 2.5 = ASM$_{20}$ | |
| | ODN A' | A' = S | |
| 1. | none | 0.35 | |
| 2. | 4, 6, 12, 19 | ND = M$_3$ = SM$_p$ | |
| 3. | 11, 21 | 75 = M$_4$ = SM$_x$ | |
| 4. | 4 | 0.4 | |
| 5. | 6 | 42 | |
| 6. | 11 | 1.7 | |
| 7. | 12 | 67 | |
| 8. | 19 | 1 | |
| 9. | 21 | 37 | |
| 10. | 6, 19 | 1 | |

TABLE 10

| | | SUBSTITUTION POSITIONS | | |
|---|---|---|---|---|
| | | 5 mC | 5 FC | RATE |
| A(AS) | 1. | none | none | 1 |
| AM$_x$(M$_2$) | 2. | 7, 11, 17 | none | 128 |
| | 3. | 7, 11, 17 | 5, 12, 18, 20 | ND |
| | 4. | 7, 11, 17 | 5 | 170 |
| | 5. | 7, 11, 17 | 12 | 165 |
| | 6. | 7, 11, 17 | 18 | 2 |
| | 7. | 7, 11, 17 | 20 | 168 |
| ASM$_5$ | 8. | 5 | none | 150 |
| | 9. | 5 | 18 | 1 |
| | 10. | 5 | 20 | 152 |

TABLE 10-continued

| | | SUBSTITUTION POSITIONS | | |
|---|---|---|---|---|
| | | 5 mC | 5 FC | RATE |
| ASM$_7$ | 11. | 7 | none | 130 |
| ASM$_7$F$_{18}$ | 12. | 7 | 18 | 3.2 |
| | 13. | 7 | 20 | 160 |

What is claimed is:

1. A substrate selective for detection of mammalian 5-C-DNA methyltransferase in the presence of bacterial 5-C-DNA methyltransferase, said substrate comprising a single strand of oligomeric DNA (ODN) which contains at least one cytosine or 5-fluorocytosine residue, each of which is followed in linkage to a guanine residue and which contains at least one 5-methylcytosine residue, said oligomeric DNA containing from 12 to 50 nucleotides and being capable of forming loop structures containing a cytosine-guanine cross bond at the beginning of the loop.

2. The substrate of claim 1 wherein the ODN contains from 12 to 50 bases and at least one cytosine-guanine linkage where the cytosine may be cytosine, 5-methylcytosine or 5-fluorocytosine and at least one cytosine group is 5-methylcytosine.

3. The substrate of claim 1 wherein the substrate also contains at least one 5-fluorocytosine.

4. The oligomeric DNA strand ATTGNGCATTCNG-GATCNGNGATC (Seq. ID #8) where N is 5-methylcytosine.

5. The oligomeric DNA strand GATRGRGGATCRG-GAATGRGCAAT (Seq. ID #20) where R is cytosine or 5-fluorocytosine.

6. The oligomeric DNA strand ATTGCGNATTNCGGAT-NRGCGATC (Seq. ID #1) where N is 5-methylcytosine and where R is cytosine or 5-fluorocytosine.

7. The double stranded oligomer formed by oligomeric DNA strands ATTGCGNATTCCGGATCRGCGATC (Seq. ID #2) and ATTGNGCATTCCGGATCRGCGATC (Seq. ID #3) where N is 5-methylcytosine and where R is cytosine or 5-fluorocytosine.

8. A method for measuring the presence of mammalian 5-C-DNA methyltransferase which comprises contacting a sample containing 5-C-DNA methyl transferase with the substrate of claim 1.

9. A method for measuring the presence of mammalian 5-C-DNA methyltransferase which comprises contacting a sample containing 5-C-DNA methyl transferase with the substrate of claim 2.

10. A method for measuring the presence of mammalian 5-C-DNA methyltransferase which comprises contacting a sample containing 5-C-DNA methyl transferase with the substrate of claim 3.

11. A method for inhibiting mammalian 5-C-DNA methyltransferase which comprises contacting a sample containing 5-C-DNA methyl transferase with the substrate of claim 1.

12. A method for inhibiting mammalian 5-C-DNA methyltransferase which comprises contacting a sample containing 5-C-DNA methyl transferase with the substrate of claim 2.

13. A method for inhibiting mammalian 5-C-DNA methyltransferase which comprises contacting a sample containing 5-C-DNA methyl transferase with the substrate of claim 3.

14. The oligomeric DNA strand ATTGCGNATTCCG-GATCRGCGATC (Seq. ID #2).

15. The oligomeric DNA strand ATTGNGCATTCCG-GATCRGCGATC (Seq. ID #3).

16. A method for measuring the presence of mammalian 5-C-DNA methyltransferase which comprises contacting a sample containing 5-C-DNA methyltransferase with the substrate of claim 14.

17. A method for measuring the presence of mammalian 5-C-DNA methyltransferase which comprises contacting a sample containing 5-C-DNA methyltransferase with the substrate of claim 15.

18. A method for inhibiting mammalian 5-C-DNA methyltransferase which comprises contacting a sample containing 5-C-DNA methyltransferase with the substrate of claim 14.

19. A method for inhibiting mammalian 5-C-DNA methyltransferase which comprises contacting a sample containing 5-C-DNA methyltransferase with the substrate of claim 15.

* * * * *

SEQUENCE LISTING ( 1 ) GENERAL INFORMATION:

( i i i ) NUMBER OF SEQUENCES: 22

( 2 ) INFORMATION FOR SEQ ID NO: 1:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 1:

ATTGCGNATT NCGGATNRGC GATC                   24

( 2 ) INFORMATION FOR SEQ ID NO: 2:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 2:

ATTGCGNATT CCGGATCRGC GATC                   24

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

(vi) ORIGINAL SOURCE:
              (A) ORGANISM:
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:
              (A) LIBRARY:
              (B) CLONE:

(viii) POSITION IN GENOME:
              (A) CHROMOSOME/SEGMENT:
              (B) MAP POSITION:
              (C) UNITS:

(ix) FEATURE:
              (A) NAME/KEY:
              (B) LOCATION:
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) ISSUE:
              (F) PAGES:
              (G) DATE:
              (H) DOCUMENT NUMBER:
              (I) FILING DATE:
              (J) PUBLICATION DATE:
              (K) RELEVANT RESIDUES IN SEQ ID NO:

(ix) SEQUENCE DESCRIPTION: SEQ ID NO: 3:

ATTGNGCATT CCGGATCRGC GATC        24

(2) INFORMATION FOR SEQ ID NO: 4:

(i) SEQUENCE CHARACTERISTICS:
              (A) LENGTH: 24
              (B) TYPE: nucleic acid
              (C) STRANDEDNESS: both
              (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
              (A) ORGANISM:
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:
              (A) LIBRARY:
              (B) CLONE:

(viii) POSITION IN GENOME:
              (A) CHROMOSOME/SEGMENT:
              (B) MAP POSITION:
              (C) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( i x ) SEQUENCE DESCRIPTION: SEQ ID NO: 4:

ATTGNGCATT CNGGATCNGN CATC          24

( 2 ) INFORMATION FOR SEQ ID NO: 5:

( i ) SEQUENCE CHARACTERISTICS:
    ( A ) LENGTH: 24
    ( B ) TYPE: nucleic acid
    ( C ) STRANDEDNESS: both
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

-continued ( i x ) SEQUENCE DESCRIPTION: SEQ ID NO: 5:

TAARGCGTAA GGRCTAGGRG GTAG 24

( 2 ) INFORMATION FOR SEQ ID NO: 6:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 6:

TAACGCGTAA GGCCTAGGCG CTAG 24

( 2 ) INFORMATION FOR SEQ ID NO: 7:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(ix) SEQUENCE DESCRIPTION: SEQ ID NO: 7:

ATTGCGCATT CCGGATCCGC GATC        24

(2) INFORMATION FOR SEQ ID NO: 8:

(i) SEQUENCE CHARACTERISTICS:
(A) LENGTH: 24
(B) TYPE: nucleic acid
(C) STRANDEDNESS: both
(D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

```
        ( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( i x ) SEQUENCE DESCRIPTION: SEQ ID NO: 8:

ATTGNGCATT  CNGGATCNGN  GATC                    24

( 2 ) INFORMATION FOR SEQ ID NO: 9:

( i ) SEQUENCE CHARACTERISTICS:
                ( A ) LENGTH: 24
                ( B ) TYPE: nucleic acid
                ( C ) STRANDEDNESS: both
                ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:
```

( i x ) SEQUENCE DESCRIPTION: SEQ ID NO: 9:

ATTGCGNATT NCGGATNCGC GATC          24

( 2 ) INFORMATION FOR SEQ ID NO: 10:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO:10:

GATNGCGGAT CCGGAATGCG CAAT          24

( 2 ) INFORMATION FOR SEQ ID NO: 11:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( i x ) SEQUENCE DESCRIPTION: SEQ ID NO: 11:

GATCGNGGAT CCGGAATGCG CAAT                    2 4

( 2 ) INFORMATION FOR SEQ ID NO: 12:

( i ) SEQUENCE CHARACTERISTICS:
                    ( A ) LENGTH: 24
                    ( B ) TYPE: nucleic acid
                    ( C ) STRANDEDNESS: both
                    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(ix) SEQUENCE DESCRIPTION: SEQ ID NO: 12:

GATCGCGGAT NCGGAATGCG CAAT    24

(2) INFORMATION FOR SEQ ID NO: 13:

(i) SEQUENCE CHARACTERISTICS:
    (A) LENGTH: 24
    (B) TYPE: nucleic acid
    (C) STRANDEDNESS: both
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

( i x ) SEQUENCE DESCRIPTION: SEQ ID NO: 13:

GATCGCGGAT CNGGAATGCG CAAT                2 4

( 2 ) INFORMATION FOR SEQ ID NO: 14:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 14:

GATCGCGGAT CCGGAATGNG CAAT                2 4

( 2 ) INFORMATION FOR SEQ ID NO: 15:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY:
      ( B ) LOCATION:
      ( C ) IDENTIFICATION METHOD:
      ( D ) OTHER INFORMATION:

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO:

( i x ) SEQUENCE DESCRIPTION: SEQ ID NO: 15:

ATTGCGNATT CCGGATCCGC GATC      24

( 2 ) INFORMATION FOR SEQ ID NO: 16:

( i ) SEQUENCE CHARACTERISTICS:
      ( A ) LENGTH: 24
      ( B ) TYPE: nucleic acid
      ( C ) STRANDEDNESS: both
      ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( i x ) SEQUENCE DESCRIPTION: SEQ ID NO: 16:

ATTGCGNATT CCGGATCNGC GATC    24

( 2 ) INFORMATION FOR SEQ ID NO: 17:

( i ) SEQUENCE CHARACTERISTICS:
    ( A ) LENGTH: 24
    ( B ) TYPE: nucleic acid
    ( C ) STRANDEDNESS: both
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( i x ) SEQUENCE DESCRIPTION: SEQ ID NO: 17:

ATGGGATCCC ATGGGTTNCC NATC    24

( 2 ) INFORMATION FOR SEQ ID NO: 18:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 18:

ATTGCGNATT CCGGATCCGC GATC    24

( 2 ) INFORMATION FOR SEQ ID NO: 19:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( i x ) SEQUENCE DESCRIPTION: SEQ ID NO: 19:

ATTGCGNATT CCGGATCCGC GATC                    2 4

( 2 ) INFORMATION FOR SEQ ID NO: 20:

( i ) SEQUENCE CHARACTERISTICS:
            ( A ) LENGTH: 24
            ( B ) TYPE: nucleic acid
            ( C ) STRANDEDNESS: both
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(ix) SEQUENCE DESCRIPTION: SEQ ID NO: 20:

GATRGRGGAT CRGGAATGRG CAAT                24

(2) INFORMATION FOR SEQ ID NO: 21:

(i) SEQUENCE CHARACTERISTICS:
                (A) LENGTH: 24
                (B) TYPE: nucleic acid
                (C) STRANDEDNESS: both
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

( i x ) SEQUENCE DESCRIPTION: SEQ ID NO: 21:

ATGACGCACC TCGTTGACGC GCTA                24

( 2 ) INFORMATION FOR SEQ ID NO: 22:

( i ) SEQUENCE CHARACTERISTICS:
        ( A ) LENGTH: 24
        ( B ) TYPE: nucleic acid
        ( C ) STRANDEDNESS: both
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( i x ) SEQUENCE DESCRIPTION: SEQ ID NO: 22:

ATTGCGCTAC TCGGATCCGG CCAT                24